(12) United States Patent
Gallagher et al.

(10) Patent No.: US 6,998,470 B1
(45) Date of Patent: Feb. 14, 2006

(54) PROCESS FOR LARGE-SCALE ISOLATION AND PURIFICATION OF HYPOTHALAMIC INHIBITORY FACTOR

(75) Inventors: Rex T. Gallagher, Beverly, MA (US); Garner T. Haupert, Jr., Littleton, MA (US)

(73) Assignees: Bion, Inc., Cambridge, MA (US); The General Hospital Corp., Boston, MA (US)

( * ) Notice: Subject to any disclaimer, the term of this patent is extended or adjusted under 35 U.S.C. 154(b) by 0 days.

(21) Appl. No.: 09/506,246

(22) Filed: Feb. 17, 2000

Related U.S. Application Data (63) Continuation of application No. 08/866,706, filed on May 30, 1997, now abandoned.

(51) Int. Cl.
C07K 1/00 (2006.01)
C07K 14/00 (2006.01)
C07K 16/00 (2006.01)
C07K 17/00 (2006.01)

(52) U.S. Cl. .................. 530/412; 530/413; 530/414; 530/417

(58) Field of Classification Search ............... 530/412, 530/413, 414, 417
See application file for complete search history.

(56) References Cited

U.S. PATENT DOCUMENTS

| 4,551,426 A | 11/1985 | Freytag et al. ............... 435/7 |
| 4,665,019 A | 5/1987 | Hamlyn et al. ............... 435/21 |
| 4,780,314 A | 10/1988 | Graves ........................ 424/95 |
| 4,897,465 A | 1/1990 | Cordle et al. ............... 530/387 |
| 5,164,296 A | 11/1992 | Blaustein et al. ........... 435/7.24 |
| 5,429,928 A | 7/1995 | Blaustein et al. ........... 435/7.24 |
| 5,716,937 A | 2/1998 | Haupert, Jr. ................ 514/25 |

FOREIGN PATENT DOCUMENTS

WO   WO92/04047   3/1992

OTHER PUBLICATIONS

Sergio, B. et al., "Effects of an Endogenous Ouabainlike Compound on Heart and Aorta", *Hypertension*, 17(6): Part 2:944-950 (1991).
Mathews, W.R. et al., "Mass Spectral Characterization of an Endogenous Digitalis-Like Factor From Human Plasma", *Hypertension*, 17(6): Part 2:930-935 (1991).
Ludens, J.H. et al., "Purification of an Endogenous Digitalis-like Factor From Human Plasma for Structural Analysis", *Hypertension*, 17(6): Part 2: 923-929 (1991).
Hamlyn, J.M. et al., "Identification and Characterization of a Ouabain-like Compound from Human Plasma", *Proc. Natl. Acad. Sci. USA*, 88:6259-6263 (1991).
Haber, E. and Haupert, Jr., G.T., "The Search for a Hypothalamic Na, K-ATPase Inhibitors", *Hypertension*, 9: 315-324 (1987).
Haupert, Jr., G.T., "Overview: Physiological Inhibitors of Na, K-ATPase Concept and Status", *The $Na^+, K^+$ Pump Part B: Cellular Aspects*, 297-320 (1988).
Mudgett-Hunter, M. et al., "High-Affinity Monoclonal Antibodies to the Cardiac Glycoside, Digoxin", *J. Immunol.*, 129(3):1165-1172 (1982).
Carilli, C.T. et al., "Hypothalamic Factor Inhibits the (Na, K)ATPase from the extracellular Surface", *J. Biol.Chem.*, 260(2):1027-1031 (1985).
Janssens, S.P. et al., "Hypothalamic $Na^+$, $K^+$-ATPase Inhibitor Constricts Pulmonary Arteries of Spontaneously Hypertensive Rats", *J. Cardio. Pharm.*, 22(Suppl. 2):S42-S46 (1993).
Haupert, Jr., G.T. and Sancho. J.M., "Sodium transport inhibitor from bovine hypothalamus", *Proc. Natl. Acad. Sci. USA*, 76(9):4658-4660 (1979).
Haupert, Jr., G.T. et al., "Hypothalamic sodium-transport inhibitor is a high-affinity reversible inhibitor of $Na^+$-$K^+$-ATPase", reprint from *Am. Physiol. Soc*, 247:F919-F924 (1984).
Mirsalikhova, N.M. et al., "Some Features of the Inhibition of $Na^+$, $K^+$-ATPase in Heart Muscle by Cardiotonic Glycosides", *Inst. Biochem. and Inst. Chem. Plant Subst., Academy of Sciences of the Urbek SSR*, Tashkent, USSR, p. 269-275.
Pitts, R.F., "Chapter 5, Clearance and Rate of Glomerular Filtration", *Physiology of the Kidney and Body Fluids* (Year Book Medical Publishers Inc., 3rd Edition, Chicago, IL): 60-63.

(Continued)

Primary Examiner—Christopher S. F. Low
Assistant Examiner—C. Delacroix-Muirheid
(74) Attorney, Agent, or Firm—Hamilton, Brook, Smith & Reynolds, P.C.

(57) ABSTRACT

The present invention relates to a method of isolating and/or purifying hypothalamic inhibitory factor (HIF) from a sample (e.g., tissue fluid) containing HIF. The present invention provides for isolation of large amounts of HIF using diafiltration, solid phase extraction and immunoaffinity techniques. In one embodiment, the invention relates to a method of purifying hypothalamic inhibitory factor from a sample containing hypothalamic inhibitory factor comprising subjecting the sample to diafiltration, solid phase extraction and immunoaffintiy chromatography. In a particular embodiment, the invention relates to subjecting the sample to diafiltration to produce a diafiltrate of HIF; subjecting the diafiltrate to a first solid phase extraction (SPE) to produce a first fraction of HIF; subjecting the first fraction to immunoaffinity chromatography, wherein an antibody which binds to HIF is coupled to an immunoaffinity column, to produce a second fraction of HIF; subjecting the second fraction of HIF to reverse phase HPLC chromatography to produce a third fraction of HIF; and recovering purified HIF from the third fraction.

40 Claims, 3 Drawing Sheets

OTHER PUBLICATIONS

Mudgett-Hunter, M. et al., "Binding and Structural Diversity Among High-Affinity Monoclonal Anti-Digoxin Antibodies", *Mol. Imunol., 22(4)*:477-488 (1985).

Smith, T.W. et al., "Treatment of Life-Threatening Digitalis Intoxication with Digoxin-Specific Fab Antibody Fragments", *The New England Journal of Medicine, 307(22)*: 1357-1362 (1982).

Smith, T.W. et al., "Reversal of Advanced Digoxin Intoxication with Fab Fragments of Digoxin-Specific Antibodies", *The New England Journal of Medicine, 294(15)*:797-800 (1976).

Hallaq, H.A. and Haupert, Jr., G.T., "Positive inotropic effects of the endogenous $Na^+/K^+$-transporting ATPase Inhibitor form the hypothalamus,", *Proc. Natl. Acad. Sci. USA, 86*:10080-10084 (1989).

Axelrod, J., "J. Methylation reactions in the Formation and Metabolism of Catecholamines and Other Biogenic Amines", *Pharm. Rev., 18(1)*: Part I:95-113 (1966).

Thomas, R. et al., "Synthesis and Biological Activity of Semisynthetic Digitalis Analogs", *J. Pharm. Sci., 63(11)*: 1649-1683 (1974).

Hoffman, B.F. and Bigger, Jr., J.T., "Chapter 34: Digitalis and Allied Cardiac Glycosides", *The Pharmacological Basics for Therapeutics*, (NY: Pergamon Press):814-839 (1990).

Haupert, Jr., G.T. et al. "Target Organ Sensitivity to an Endogenous Na, K-ATpase Inhibitor from Hypothalamus", *Kidney Int., 31*:435A (1987).

Weinberg, U. et al., "Identification and Preliminary Characterization of Two Human Digitalis-Like Substances that are Structurally Related to Digoxin and Ouabain", *Biochem. & Biophys. Res. Comm., 188*(3):1024-1029 (1992).

Tamura, M. et al., "Isolation and Characterization of a Specific Endogenous $Na^+$, $K^+$-ATPase Inhibitor from Bovine Adrenal", *Biochem., 27*:4244-4253 (1988).

Schoner, W. et al., "Purification and Properties of Endogenous Ouabain-like Substances from Hemofiltrate and Adrenal Glands", *J. Cardiovas. Pharm., 22(Suppl. 2)*: S29-S31 (1993).

Lewis, L.K. et al., "Ouabain Is Not Detectable in Human Plasma", *Hypertension, 24*(5):549-555 (1994).

Valdes, Jr., R. & Graves S.W. "Protein Binding of Endogenous Digoxin-Immunoactive Factors in Human Serum and Its Variation with Clinical Condition", *J. Clin. Endoc. Metab., 60*(6):1135-1143 (1985).

Illescas, M. et al., "Complete purification of two identical $Na^+$-pump inhibitors isolated from bovine hypothalamus and hypophysis", *FEBS Let., 261*(2):436-440 (1990).

Zhao,N. et al., "Na,K-ATPase Inhibitors from Bovine Hypothalamus and Human Plasma Are Different from Ouabain: Nanogram Scale CD Structural Analysis", *Biochem., 34*:9893-9896 (1995).

Tymiak et al., "Physicochemical Characterization of a Ouabain Isomer Isolated from Bovine Hypothalamus", *Proc. Natl. Acad. Sci., 90*:8189-8193 (1993).

Nakanishi et al., "Search for an Endogenous Mammalian Cardiotonic Factor", *Saponins Used in Traditional and Modern Medicine*, pp:219-224 (1996).

Anner et al., "Hypothalamic $Na^+$-$K^+$-ATPase Inhibitor Characterized in Two-Sided Liposomes Containing Pure Renal $Na^+$-$K^+$-ATPase", *Am. J. Physiol., 258 (Renal Fluid Electrolyte Physiol., 27)*:F144-F153 (1990).

Montali, U., et al., "Purification of Endogenous Digitalis-Like Factor(s) from Cord Blood of Neonate by Immunoaffinity Chromatography," *Biochem. Int;25*:853-859 (1991).

PROCESS FOR LARGE-SCALE ISOLATION AND PURIFICATION OF HYPOTHALAMIC INHIBITORY FACTOR

RELATED APPLICATION(S)

This application is a Continuation of U.S. application Ser. No. 08/866,706, filed May 30, 1997, now abandoned, entitled "Process for Large-Scale Isolation and Purification of Hypothalamic Inhibitory Factor", the entire teachings of which are incorporated herein by reference.

GOVERNMENT SUPPORT

This work was supported by NIH SBIR grant R43 HL57051 and NIH grant R01 HL 52282. Therefore, the government has certain rights in the invention.

BACKGROUND OF THE INVENTION

Hypothalamic inhibitory factor (HIF), an isomer of ouabain, is a physiologic inhibitor of membrane-bound $Na^+$, $K^+$-activated adenosine triphosphate ($Na^+$, $K^+$-ATPase) and produces a positive inotropic effect on cardiac cells. Positive inotropic effect means that the contractility of the cardiac cells is enhanced in a dose-dependent manner. HIF can be administered to a mammalian host to treat cardiac malfunction (e.g., congestive heart failure, paroxysmal atrial tachycardia, atrial fibrillation and flutter). Use of HIF for treating cardiac malfunction is further described in U.S. patent application Ser. No. 08/338,264, filed Nov. 10, 1994.

HIF has been purified to homogeneity using an affinity chromatography method in which purified canine renal $Na^+$, $K^+$-ATPase is coupled to paramagnetic particles through a glutaraldehyde bridge (Tymiak, A. A., et al. *Proc. Natl. Acad. Sci., USA*, 90:8189–8193 (1993)). The enzyme immobilizes bound HIF in the presence of $Mg^{++}$ and inorganic phosphorous with high affinity, and after washing away contaminating materials, HIF is eluted from the affinity column by chelating $Mg^{++}$ with EDTA. With a subsequent HPLC step, this technique produced enough pure HIF to allow structure determination and the differentiation of HIF from ouabain (Tymiak, A. A., et al. *Proc. Natl. Acad. Sci., USA*, 90:8189–8193 (1993)). Unfortunately, losses at the affinity step are substantial, with activity recovery averaging only 30%. Also, the method is laborious in the sense that pure enzyme needs to be repeatedly prepared from fresh canine renal medulla.

Thus, a need exists for an improved method of isolating and/or purifying HIF. In particular, there is a need for large-scale preparative methods for purifying HIF.

SUMMARY OF THE INVENTION

The present invention relates to a method of isolating and/or purifying hypothalamic inhibitory factor (HIF) from a sample (e.g., tissue fluid) containing HIF. The present invention provides for isolation of large amounts of HIF using diafiltration, solid phase extraction and immunoaffinity techniques; preferably all three techniques are used. However, it should be recognized that each of the steps of the process could be used alone or in any combination. For example, diafiltration, the solid phase extraction and the immunoaffinity technique described herein may be used alone or in combination with other known methods to purify and/or isolate HIF from an appropriately prepared sample, e.g., a sample chromatographically treated. In one embodiment, the invention relates to a method of purifying hypothalamic inhibitory factor from a sample containing hypothalamic inhibitory factor comprising subjecting the sample to diafiltration, solid phase extraction and immunoaffintiy chromatography. In a particular embodiment, the invention relates to subjecting the sample to diafiltration to produce a diafiltrate of HIF; subjecting the diafiltrate to a first solid phase extraction (SPE) to produce a first fraction of HIF; subjecting the first fraction to immunoaffinity chromatography, wherein an antibody which binds to HIF is coupled to an immunoaffinity column, to produce a second fraction of HIF; subjecting the second fraction of HIF to a second SPE to produce a third fraction of HIF; and recovering purified HIF from the third fraction.

In one embodiment, the present invention relates to a method of purifying HIF wherein a tissue slurry from a sample comprising HIF is prepared. A retentate of the tissue slurry, which includes HIF is then prepared. The retentate is diafiltered to produce a diafiltrate which includes HIF which is chromatographically treated using solid phase extraction. Immunoaffinity chromatography is then performed on the HIF using an antibody (e.g., a monoclonal antibody) which binds to HIF. Following immunoaffinity chromatography, reverse phase high pressure liquid chromatography (RPHPLC) can be performed to produce further purified HIF. An example of a monoclonal antibody which binds HIF is 26-10 (Mudgett-Hunter, M., et al., *J. Immunol.*, 129: 1165–1172 (1982)).

A deposit of hybridoma 26-10 has been made under the terms of the Budapest Treaty on Mar. 31, 1982 on behalf of Massachusetts General Hospital (the General Hospital Corporation), 55 Fruit Street, Boston, Mass., 02114 at the American Type Culture Collection, 10801 University Boulevard, Manassas, Va. 20110–2209 under Accession Number HB-8120, and is available for distribution.

In another embodiment, the invention relates to a method of purifying HIF wherein tangential diafiltration is performed on a sample comprising HIF to produce a diafiltrate permeate which includes the HIF. SPE is then performed on the diafiltrate permeate to produce a concentrate of HIF. Following SPE, immunoaffinity chromatography is performed on the concentrate using an antibody having affinity for HIF to produce a HIF-containing fraction. RPHPLC, or a similar technique, preformed on the HIF fraction follows which results in the production of purified HIF.

The present invention also relates to a method of purifying HIF wherein a tissue comprising HIF is blended to form a tissue slurry, which is centrifuged to produce a retentate comprising the HIF. The retentate is tangentially diafiltered to produce a diafiltrate permeate comprising the HIF. The diafiltrate permeate is chromatographically treated by SPE employing an acetonitrile elution and a silica packing to produce a first HIF fraction in acetonitrile. The first fraction is concentrated and then chromatographically treated by immunoaffinity chromatography employing a glycine elution and a resin packing, wherein an antibody which binds to HIF is coupled to the resin, to produce a fraction of HIF in glycine. The fraction of HIF in glycine is chromatographically treated by RPHPLC employing an acetonitrile gradient elution and a silica packing to produce a second HIF fraction in acetonitrile. The acetonitrile is then evaporated from the second HIF fraction thereby producing purified HIF.

Purification of HIF using the methods described herein provides for at least a 15-fold increase in yield of pure HIF over the prior art processes.

DETAILED DESCRIPTION OF THE INVENTION

The present invention relates to a method of purifying HIF from a sample (e.g., tissue or fluid) containing HIF. The isolation and purification scheme for HIF is based in part on the discovery that the following combination of key properties of HIF: that HIF is a small, low molecular weight molecule (MW 584) and highly water soluble, allows exploitation of purifying HIF using any, and preferably all or a combination of the following diafiltration, solid phase extraction and immunoaffinity on an industrial scale. In a particular embodiment, tangential diafiltration technology, coupled in 'tandem' to solid phase extraction is used to provide an efficient isolation procedure to remove the HIF from the tissue or fluid source. Subsequent purification by immunoaffinity chromatography, optionally followed by reverse phase high performance liquid chromatography, yields purified HIF.

As defined herein, purified HIF refers to HIF which is substantially free of or isolated from other tissue or fluid protein components and contaminants. In addition, the purified HIF of the present invention has at least 40% activity recovery. Preferably, the purified HIF has about 50–75% activity recovery, more preferably the purified HIF has about 75–90% activity recovery and most preferably, the purified HIF has about 90–95% activity recovery. As defined herein, "activity recovery" of HIF is the activity of HIF as measured indirectly by, for example a biological assay such as specific inhibition of $Na^+$-$K^+$-ATPase pump activity in human erythrocytes, or as measured directly, for example, by UV absorbance following HPLC chromatography.

HIF can be purified from any mammalian (e.g., bovine, murine, human) sample, such as a tissue or fluid source, in which HIF is present using the methods described herein. For example, as demonstrated herein, HIF can be isolated from bovine hypothalamus. Other suitable samples which can be used in the methods of the present invention include, but are not limited to, blood, blood plasma, urine, muscle, placental tissue, lymph, cerebrospinal fluid, cardiac tissue, adrenal tissue, pituitary glands, kidney, and/or renal tissue. It is understood that the HIF source can be from a freshly collected tissue or fluid sample or from an old sample previously maintained, for example, in a frozen state.

In the embodiment in which the sample is blood, at or soon after collection, the blood can be mixed with at least one anticoagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution.

As described in the exemplification, in one embodiment of the present invention a slurry is prepared from the tissue or fluid source from which the HIF is being purified. Suitable methods for preparing a slurry include blending the tissue or fluid with a suitable water miscible solvent (e.g., alcohol, methanol, ethanol, glycol, dimethylformamide, acetone, dimethylsulfoxide, acetonitrile and other such solvents). It is understood that other methods generally known in the art for preparing a slurry from a tissue or fluid sample can be employed. For example, a homogenizer, such as a Waring blender can be used.

Following preparation of the slurry, a retentate of the slurry which includes HIF is prepared by decanting a supertanant. Centrifugation of the slurry can be used to obtain a retentate which includes HIF. Optionally, the slurry can be centrifuged at, for example, about 4000 G for about 25 minutes. It is preferred that the retentate obtained from the tissue slurry contains a minimum concentration of about 500 units bioactivity HIF which is approximately 219 ng HIF per kg starting tissue. It is understood that other methods generally known in the art for preparing a retentate from a slurry can be employed to obtain HIF in the retentate. For example, filtration can also be used to obtain a retentate which includes HIF.

Ultrafiltration can then be used on the retentate which includes HIF to remove large and/or high molecular weight components. In ultrafiltration procedures on biological extracts, concern arises from the potential of proteins that might bind generally or specifically to the small amounts of desired solute molecules, such as HIF molecules, in the very complex soup of biomolecules that constitutes the extract. Literature descriptions of purification procedures for endogenous digitalis-like factor (EDLF) and ouabain-like compounds (OLC) suggest that such a mechanism could well operate in the case of ultrafiltration purification procedures for HIF from slurry preparations (Valdes, R. Jr., et al, *J. Clin. Endocrinol. Metab.*, 60:1135–1143 (1985)). In a preferred embodiment, continuous diafiltration can be used to circumvent the problem associated with ultrafiltration, both for solutions and for particulate-laden preparations.

Diafiltration is performed on tissue or fluid samples in which HIF is present to remove larger or high molecular weight tissue components such as proteins, polysaccharides, peptides, lipoproteins and nucleic acids, with a molecular weight above about 3000 daltons. Acceptable diafilters for use in the present invention include, for example, filters made by Pall (e.g., Pall Filtron, catalogue number 0S003G05, Omega 3 KD Open Channel 30 mil 4 $ft^2$ cassette), Millipore and A/G Technology. Preferred characteristics of the diafilters for use in the present invention include narrow pore-size distribution, high flow rates, stability against biological degradation, stability against organic solvents (e.g, methanol, ethanol), good permeability performance and/or good membrane recovery after cleaning. In a particular embodiment, the diafilter is such that protein binding to the surface and interstitial structure of the membrane filter occurs to a minimum (less surface fouling). Preferred diafilter polymers include, for example, polyether sulfone (e.g., a modified Pall polyether sulfone membrane), cellulose and/or regenerated cellulose filters. The diafiltration step can be performed using numerous techniques.

Diafiltration is the fractionation process of "washing" smaller molecules through an ultrafiltration membrane, leaving larger molecules in the retentate. The process of continuous diafiltration is achieved by adding solvent to the retentate at the same rate as solvent and small molecules pass into the filtrate. The diafiltration volume is the volume equal to the initial process sample or feed volume in which the molecule of interest occurs. The number of diafiltration volumes required for a successful fractionation depends on several factors, most particularly on how readily the molecule of interest is retained or permeates through the membrane. For molecules that have no membrane retention (retention=0%, i.e. fully permeates the membrane) such as salts and solvents, 7 diafiltration volumes are required for 99.9% removal from the retentate. For a molecule that is retained 25%, 9 volume exchanges are required (Membrane Separation Products catalog, (1995/1996) Filtron Corporation, Northborough, Mass. 01532, see pages 9, 10, & Table 2). For purification of HIF using the methods described herein, the number of diafiltration volumes (DVs) used can range from about 5 DVs to about 30 DVs. In a preferred embodiment, the number of DVs used can range from about 7 DVs to about 20 DVs, and most preferred can range from about 15 DVs to about 20 DVs.

Solvents for use in diafiltration can be any solvent which is compatible with the aqueous solvent system used in the diafiltration process and include, for example, deionized water ($DIH_2O$), sodium chloride, sodium acetate and phosphate buffers (e.g., Tris).

In one embodiment, the diafiltration is performed using a continuous diafiltration method. In a preferred embodiment, tangential diafiltration is used. Tangential diafiltration produces a "sweeping" action across the membrane surface; this sweeping action keeps the retained macromolecules in the retentate phase from accumulating at the membrane surface, thus minimizing concentration polarization and membrane fouling. Thus, in tangential dialysis, sample is recirculated across the top of the membrane—"tangentially" to the membrane surface—while applied pressure causes solute and small molecules to pass through the membrane.

For example, hollow fiber, spiral membrane cartridges, and open-channel membrane cartridges, which are based on tangential flow technology, can be used. In a preferred embodiment, tangential diafiltration is performed using a linear-open-channel separator. As described in the exemplification, the Pall Filtron Corporation technology of membrane "cassettes" with retentate channels processing linear-open-channel separators can be used (Membrane Separation Products catalog, (1995/1996) Filtron Corporation, Northborough, Mass. 01532, see pages 9, 10, & Table 2). The cassette technology consists of multiple layers of ultrafiltration (UF) membrane assemblies composed of sheets of UF membrane placed alternately between filtrate screen separators, and retentate screen separators, in a sandwich-like arrangement. Blocked borders on the filtrate and retentate screens direct the separated fractions to collection ports on the manifold. These cassettes allow cells and particulate matter to move freely above the membrane surface at low shear conditions without plugging. A key concept of the cassette technology is that cassettes can be stacked in multiple units, enabling large batch volumes of feed solutions and broths to be processed. Scale-up simply requires increased membrane area, obtained by adding more cassettes, and increased pump capacity. Optionally, one or more ultrafiltration steps can be performed after diafiltration or in between diafiltration steps. For example, diafiltration is performed on the supernatant as described herein. Then ultrafiltration (addition of buffer is stopped) is performed on the retentate until the retentate volume is reduced. Thereafter, diafiltration can again be commenced until the desired DV is achieved.

Following diafiltration of retentate of the sample (e.g., tissue) slurry, solid phase extraction (SPE) can be performed on the diafiltrate of HIF. It should be recognized that it may be desirable to perform SPE before and/or after diafiltration although diafiltration is preferably performed first. The solid phase extraction can be performed using numerous techniques. For example, the diafiltrate of HIF is directed into one or more SPE chromatographic columns or cartridges to further separate the HIF from other contaminants such as ions, fatty acids, phospholipids, amino acids, sugars and/or steroids. Examples of suitable media or packing of the chromatographic columns or cartridges include but not limited to reverse phase silicas (e.g., C4, C8, C12, C18), polyvinylpyrrolidone (e.g., HP-20), various cellulose derivatives (e.g., acetate cellulose) and cyclodextrins (e.g., α, β, β and derivatives thereof). In a preferred embodiment, SPE chromatographic columns or cartridges contain a silica based packing suitable to separate HIF from additional contaminants. Suitable silica based column packings include, for example, C4, C8, C12 and C18 columns.

Chromatographic columns are first pre-treated by flushing with a first eluant which facilitates HIF binding. Diafiltered HIF is then injected onto the media columns. After injecting the diafiltered HIF, the chromatographic columns are then successively washed with different eluants to produce an HIF fraction which has been further purified.

An acetonitrile/water eluant is used to remove protein etc. on the SPE chromatographic column or cartridge. In a particular embodiment, a C18 SPE technique is used to extract HIF from the large volume of aqueous permeate generated in the tangential diafiltration of the bovine hypothalamic supernatant. The SPE step captures the small amount of the desired HIF molecule in the dilute aqueous solution/slurry; elution with about 30–60% aqueous acetonitrile then yields the HIF in a highly concentrated SPE fraction.

Following SPE, the HIF fraction can be further concentrated under vacuum, for example, on a Buchi rotary evaporator and/or a Savant SpeedVac vacuum concentrator. It is understood that other methods generally known in the art for concentrating purified fractions obtained from SPE can be employed.

Affinity chromatography can then be performed on the highly concentrated SPE fraction. In one embodiment, affinity chromatography can be performed using the $Na^+$-$K^+$-ATPase inhibitor. In a preferred embodiment, immunoaffinity chromatography is performed on the HIF in a highly concentrated SPE fraction or on the HIF fraction which has been further concentrated under vacuum. In another embodiment, an HIF containing fluid or tissue sample which is free of high molecular weight tissue components is subjected to immunoaffinity chromatography. Concentrated HIF is directed onto one or more chromatographic immunoaffinity columns to produce an immunoaffinity column eluate which includes HIF further separated from other contaminants such as steroids (e.g., corticosteroids), fatty acids and other small organic molecules. Examples of suitable media or packing of the chromatographic immunoaffinity columns include various sepharose resins to which is bound an antibody which binds to HIF. In a preferred embodiment, chromatographic immunoaffinity columns contain a sepharose, polydextran carbohydrate, D-galactose, 3-6 anhydrol galactose resin or packing which can be coupled to an antibody which binds HIF facilitating further separation of HIF from additional contaminants. Suitable chromatography immunoaffinity column packings include cyanogen bromide activated Sepharose 4B resin, Sephadex 300 and Sephacryl 300.

Antibodies for use in the methods of the present invention include antibodies which bind to HIF (anti-HIF antibodies). In one embodiment, the antibody specifically recognizes HIF. In another embodiment, the antibody reversibly binds to the HIF. In a preferred embodiment, the antibody has good affinity for HIF (e.g., the affinity of monoclonal antibody 26-10) and low cross reactivity with other mammalian steroids. The binding affinity of the antibody to HIF for use in the present invention is from about $3 \times 10^{-7}$ M to about $5 \times 10^{-7}$ M. In one embodiment, the anti-HIF antibody has a binding affinity of about $3 \times 10^{-7}$ M for HIF. In a preferred embodiment the antibody for use in the methods of the present invention is a monoclonal antibody. In a particular embodiment, the monoclonal antibody is 26-10 (Mudgett-Hunter, M., et al., *J. Immunol.*, *129*:1165–1172 (1982)). Antibody fragments (e.g., Fab fragments; an HIF antibody binding fragment) can be used in the methods of the present invention. For example, an HIF binding fragment of mAb 26-10 can be used.

An antibody which binds HIF can be coupled to the immunoaffinity column packing using numerous techniques. For example, the antibody is contacted with the packing or solid phase matrix of the immunoaffinity column and a chemical molecule which crosslinks the antibody to the packing. Methods for coupling antibodies (e.g., covalently) to solid phase matrices include, for example, use of A/G beads, activated beads and/or activated antibodies. (See e.g., Antibodies, A Laboratory Manual, by Ed Harlowe and David Lane (1988), which is herein incorporated by reference).

Elution of HIF from the immunoaffinity column can be accomplished using a variety of techniques. For example, the immunoaffinity column to which is bound HIF can be treated with harsh conditions, a saturating amount of a compound which mimics the binding site and/or an agent that induces allosteric changes resulting in release of HIF. In one embodiment, a glycine elution is used to remove the HIF from the immunoaffinity column. (See e.g., *Antibodies, A Laboratory Manual*, by Ed Harlowe and David Lane (1988), Chapter 13).

In a preferred embodiment, aqueous alcohol (e.g., methanol) is used to elute HIF from the immunoaffinity column. Many proteins and enzymes are easily denatured by a variety of physio-chemical factors. Loss of "active" conformational states of such biomolecules, by unfolding of the molecules, and subsequent refolding to other (unnatural) conformations, or even complete loss of ability to refold, usually means a loss of key properties; if the ability to return to the useful conformation(s) is permanently lost, then the molecules are 'denatured' and are no longer of use. Exposure to organic solvents, including significant concentrations of alcohols, such as methanol and ethanol, is often enough to permanently denature many enzymes and proteins. However, as shown herein, in the case of affinity media prepared by immobilization of an antibody onto a stable supporting matrix, antibody stability can be achieved to moderate levels of alcohol (e.g., methanol, ethanol) concentrations in aqueous solutions.

After immunoaffinity chromatography, reverse phase high pressure liquid chromatography (RPHPLC) can be, and is preferably, performed. However, a variety of techniques can be used in place of or in addition to RPHPLC. Today, RPHPLC is the most common form of HPLC. In RPHPLC, water-containing mobile phases are used with column packings that have a hydrophobic surface layer. The immunoaffinity eluate of HIF can be directed, for example, onto one or more HPLC columns to further separate HIF. Suitable HPLC column packings include reverse phase silicas (e.g., C4, C8, C12, C18), cyclodextrins (e.g., α, β, γ and derivatives thereof), phenyl, CN and $NH_2$ packings. In a preferred embodiment, end-capped silica is used. Chromatographic columns are first pre-treated by flushing with a first column eluant which facilitates HIF binding. After injecting the immunoaffinity eluate of HIF onto the column, the chromatographic columns are then successively washed with different eluants and/or gradients to produce an HIF fraction which has been further purified.

For example, an acetonitrile gradient can then be used to remove the HIF from the RPHPLC column. In a particular embodiment, an analytical C18 HPLC column can be used as a "preparative" column at the final stage of purification. Since only μg of substance are being injected in a run, the full resolution capabilities of the column can be realized. Fractions collected from an "analytical" run, yield pure HIF, which can be determined using, for example, a characteristic UV spectrum, a bioassay and/or electrospray mass spectroscopy (ESMS). Repeat runs, and columns additional to C18, can also be used to give HIF of the highest purity.

The purification procedure described herein has several advantages over previous methods. For example, final yields of pure HIF are increased at least 15-fold. The antibody column is stable and can be reused at least ten times without loss of activity. Scale-up to accommodate larger front-end preps is easily accomplished since 26-10 can be produced in whatever quantities are needed as described below. Purified HIF of the present invention can be used to treat cardiac malfunction as further described in U.S. patent application Ser. No. 08/338,264, filed Nov. 10, 1994, which is incorporated by reference.

This invention is illustrated further by the following exemplification which is not to be construed as limiting in any way.

EXEMPLIFICATION

Example 1

Purification of HIF

Tissue is processed in a batch-mode operation, 1 Kg tissue per batch. Scale-up operations can be performed, either with additional processing lines of equipment, or with larger industrial-scale systems, readily available from the equipment suppliers.

Tissue slurry preparation:

The tissue sample of frozen bovine hypothalamus, or other animal tissue or fluid, 1 Kg, was placed in a high-speed blender (e.g. Waring, one gallon 'Commercial Heavy Duty Blender'), with 1.5 L MeOH, and blended for 3×20 seconds low, 3×20 seconds on medium and 2×20 seconds on high speed. The resulting slurry was decanted from the blender into a glass jar bath (e.g. Kimax, 7.5 L, 83/4"×10"), and the blender was then rinsed out successively with 1.0 L, then 1.5 L MeOH, the rinsing being added to the glass jar bath. The slurry was left to stir overnight at 300 rpm at 4° C.

Supernatant Preparation:

The stirred slurry was decanted into centrifuge bottles (e.g. 6×1 L, Nalgene, with screw caps), and centrifuged at 4,000 G for 25 min at 12° C. (e.g. Marathon 12KBR centrifuge). The resulting supernatant phase was poured into a glass jar bath (e.g. Kimax, as above). This supernatant phase is referred to as the "retentate".

Diafiltration:

Diafiltration was then performed on the supernatant. In one procedure, the retentate was pumped through a tangential ultrafiltration membrane system (e.g. Pall Filtron polyethersulfone (PES) membranes, Omega Cassette 3 kD Open Channel, 6-cassette stack, in a Maximate-Ext stainless steel cassette holder (or equivalent equipment), total membrane surface area=24 ft$^2$), with the pump speed and control valves adjusted for an average retentate flux of 5.5 LMH, and a retentate flow rate=200–220 ml/min; diafiltration "buffer" (=DIH$_2$O, in this application), 50 L, was fed via a peristaltic pump into the retentate jar bath, at a flow rate=permeate flow rate, so that constant volume in the retentate jar bath was maintained.

Typically, for an average filtrate flux=217 ml/min, a run takes 3.8–4.0 hours to generate 50 L filtrate (permeate). Collection of 50 L permeate gives a diafiltrate volume (DV) value of ca. 10. Transmembrane pressures required in this process are typically 3–4 psi.

The diafiltration cassette stacks and equipment were cleaned with NaOH (0.5N, 50° C.), NaOCl (400 ppm), and PBS buffer (0.1M, pH 7.0), followed by a H$_2$O wash, to return them to their original condition, prior to the next batch being processed.

In a variation of the above procedure, diafiltration was performed as follows: 1 L DIH$_2$O was added to the initial retentate slurry in the jar bath, to give an initial bath volume of ca. 5.0 L, and diafiltration was performed as above, for ca. 0.5–1.5 hr, until 5–10 L permeate was collected. Then, ultrafiltration was performed (i.e. addition of H$_2$O to the retentate jar, via the peristaltic pump, was stopped) on the retentate, until the retentate volume was reduced to 4 L. Thereafter, diafiltration was again commenced, and continued until the total permeate volume collected was 50 L.

This procedure has the advantage of exposing the membranes in the cassette stacks to a lower initial concentration of MeOH, which helps reduce a tendency for the membranes to swell and give low transmembrane flow rates, with high transmembrane pressures (TMP's).

Solid Phase Extraction of HIF from Diafiltration Permeate:

Accumulated permeate from above, containing HIF, was pumped through a C18 SPE column (Biotage Flash 75M cartridge, 7.5×15 cm, custom-packed with end-capped, high-carbon load (ca. 18–22%) C18 silica), at a flow rate of 220–280 ml/min, retaining the HIF on the column. The column was then washed with 4 L H$_2$O, then the HIF was eluted with 2 L 80% aqu ACN. Collected fractions were bioassayed to locate HIF, and HIF-containing fractions pooled and concentrated under vacuum on a Buchi rotary evaporator, and/or a Savant SpeedVac vacuum concentrator.

Purification via Affinity Chromatography with Digoxin Antibodies:

As described below, affinity purification of the HIF in the concentrate was achieved with anti-digoxin monoclonal antibody immobilized on Sepharose. The fractionation was guided by bioassay, and HPLC with UV detection.

Figure 1:
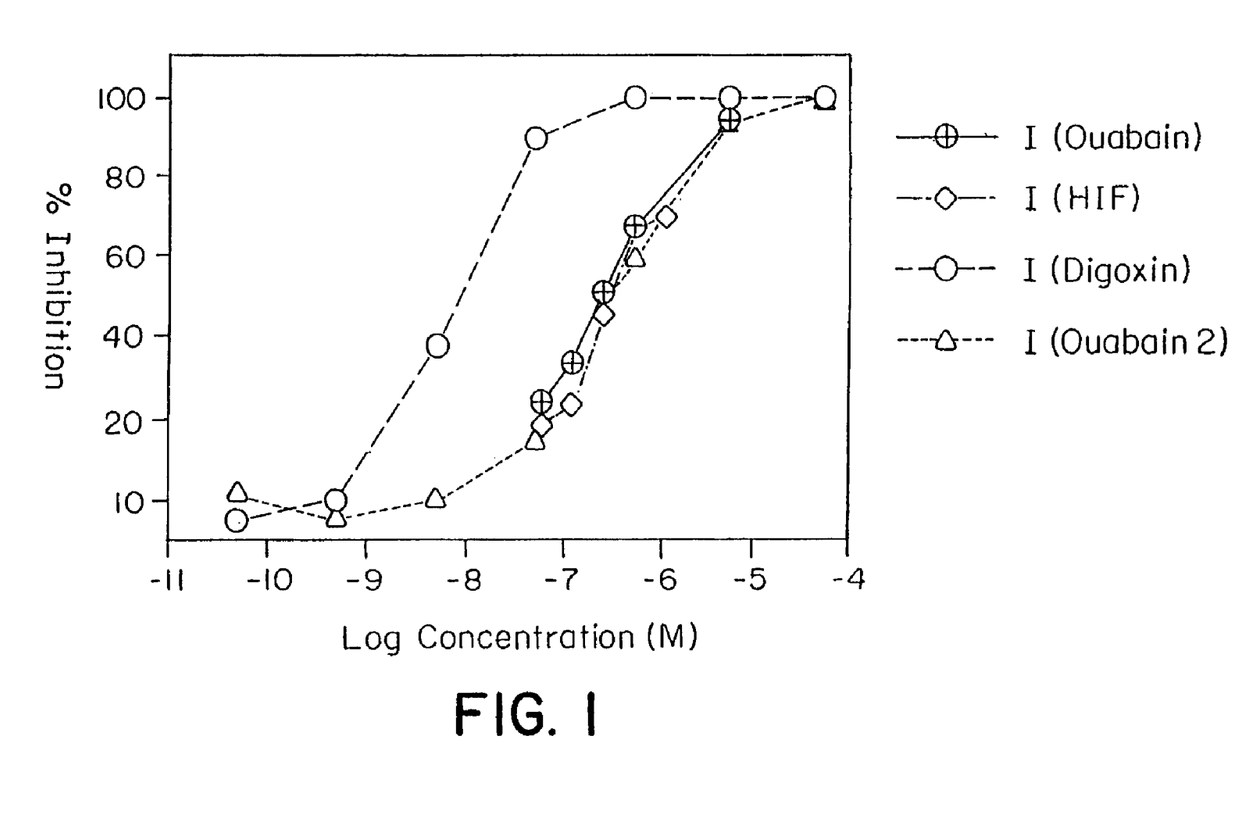
FIG. 1 is a graph of log concentration (M) versus % inhibition showing the binding curves of ouabain and HIF to monoclonal antibody 26-10.

Studies indicated that some monoclonal anti-digoxin antibodies recognized ouabain (Panka, D. J. and Margolies, M. N., *J. of Immunol.*, 132:2385–2391 (1987)). Several available anti-digoxin antibodies were studied to determine relative affinity for ouabain. In an $^{125}$I competition plate assay using goat-anti-mouse IgG Fab to bind the antibodies, it was found that one of the antibodies, 26-10 (Mudgett-Hunter M. et al., *J. Immunol.* 129:1165–1172, (1982)) bound ouabain with a relative affinity (IC$_{50}$) of 3×10$^{-7}$ M. 26-10 was then studied for binding of ouabain and HIF in side by side experiments using biologically equivalent amounts of the two inhibitors based on the standard human erythrocyte $^{86}$Rb$^+$ uptake assay. FIG. 1 shows that ouabain and HIF binding curves were virtually superimposable.

Monoclonal antidigoxin antibody 26-10 was obtained from A/J mice immunized with a digoxin-human serum albumin (Dig-HSA) conjugate and spleen cells were fused with the non-secreting murine myeloma Sp2/0 cell line (Mudgett-Hunter, M., et al. *J. Immunol.*, 129:1165–1172 (1982)). Hybridoma cells identified by radioimmunoassay (RIA) as secreting anti-digoxin antibody were cloned and grown in tissue culture and amplified in the ascites form in mice. Digoxin specific hybridoma proteins were purified from ascites by a variety of chromatographic methods, including ion-exchange chromatography on DEAE cellulose and affinity chromatography on Digoxin-BSA-Sepharose or ouabain-amine Sepharose.

Coupling of Antibody 26-10 to Sepharose-4B

Antidigoxin antibody 26-10 was coupled to cyanogen bromide activated Sepharose ("Affinity Chromatography, Principles and Methods", Pharmacia LKB Biotechnology Series). CNBr activated Sepharose 4B resin was suspended in 1 mM HCl solution. The swelled gel was washed with the same HCl solution on a sintered glass filter. After the HCl solution was sucked off and cracks appeared in the gel, the gel was then immediately transferred to the solution of antibody 26-10. The antibody solution was previously prepared by dialyzing against 0.1 M NaHCO$_3$ buffer (pH 8.3) containing 0.5 M NaCl. The coupling reaction was carried out at 4° C. with gentle shaking for 3 days; the immobilization yield was 97%. The Ab-Sepharose resin is stored in 0.1 M phosphate buffered saline (pH 7.2) containing 0.1% sodium azide (PBSA).

Elution Conditions of Affinity Column and Reuse

In pilot studies using $^3$H-ouabain, various eluants were studied to determine an optimal recovery procedure. 0.2 M glycine (pH 2.5) provides consistently efficient elution of ouabain and HIF (latter determined by bioassay units of activity before and after the chromatography). If washed and stored in PBSA at 4° C. between use, the affinity resin complex shows good stability. No obvious decrease in binding efficiency has been noted in over 10 repeated uses in the purification of HIF.

Affinity-HPLC Separation of HIF

Dried HIF from the Biotage SPE column was dissolved in 0.1 M PBS buffer (pH 7.2) and loaded onto a 10 ml Ab-resin column and incubated at 4° C. overnight. The supernatant is allowed to pass through the column and the resin was washed with PBS (15 ml×3). The affinity column was then eluted with 0.2 M glycine solution (pH 2.5, 10 ml×5).

The combined glycine elution solution was filtered and loaded onto a semi-preparative mBondapak C18 column (Waters, 10 mm, 125 Å, 19 mm×150 mm). The column was washed (6 ml/min) with deionized water eluting the glycine (UV detection at 220 nm), with continued water wash for an additional 30–40 min, followed by elution with a gradient of 0–30% acetonitrile at a flow rate of 6 ml/min. HIF elutes at 16–18 min into the gradient as detected by bioassay.

Alternatively, 1 ml columns of the affinity medium, packed in 0.1 M PBS/0.1% Na azide, were first washed free of azide with 5 ml PBS at a flow rate of 1 drop/sec. Then 1 ml of HIF solution (dissolved in 0.1 M PBS) was loaded on the column and allowed to equilibrate for 40 minutes. The column was washed with 5 ml 0.1 M PBS and 5 ml DI H$_2$O. HIF was eluted from the column with 10 ml 40% aqueous MeOH (40 MeOH:60H$_2$O) and fractions of the eluate were collected. The column was equilibrated with 5 ml 0.1 M PBS/0.1% Na azide, and stored in the cold until needed again.

Final Purification via HPLC on Analytical C18 Columns

The pooled, HIF-containing fraction was concentrated under vacuum (Buchi evaporator and/or Savant SpeedVac concentrator), and applied to an analytical C18 column, with aqueous ACN gradients at a flow rate of 1.0 ml/min. The procedure utilized a gradient program as follows: from 95% $H_2O$:5% ACN to 70% $H_2O$:30% ACN over 20 min, then to 10% $H_2O$:90% ACN over 5 min, hold for 1 min, then back to 95% $H_2O$:5% ACN over 5 min. Under these conditions, HIF has a retention time of ca. 14.2 min, identical to that of ouabain, on an Alltech Alltima C18 column, 4.6×250 mm, 3μ silica particle size. Fractions were collected and bioassayed (see above), and also monitored by UV diode-array detection, and LC/MS if desired. HIF-pure fractions are pooled and evaporated to give pure HIF.

Results

Figure 3:
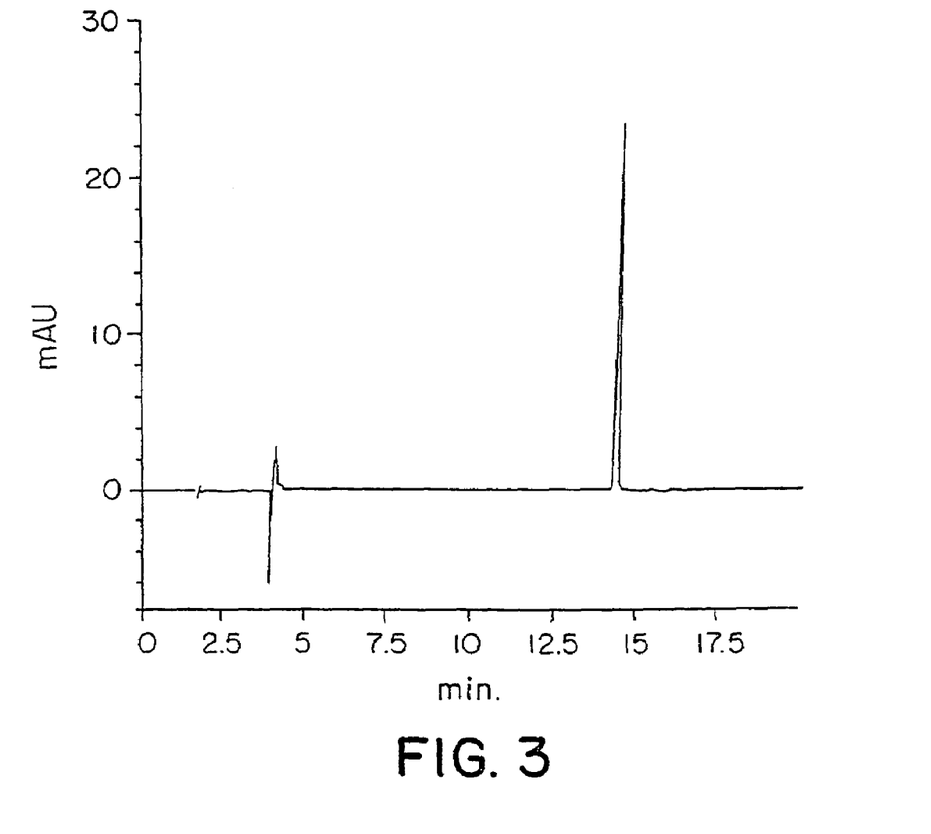
FIG. 3 is a chromatograph of analytical high pressure liquid chromatography isolation of purified HIF in which a C18 column and an acetonitrile:water gradient with UV detection at 220 nm was used.

The middling affinity of mAb 26-10 for HIF is desirable since it binds HIF, but not so avidly that elution is problematic. A method to purify HIF using mAb 26-10 coupled to cyanogen bromide activated Sepharose 4B was devised. Binding was done in phosphate buffered saline (PBS) and elution with 0.2 M glycine, pH 2.5. The eluate was chromatographed by semipreparative and then analytical C18 HPLC. Bioactivity eluted in a narrow peak (see FIG. 3), and was characterized for yield in the erythrocyte $^{86}Rb^+$ uptake assay. Table 1 shows the results of three representative experiments. As can be seen, there is a substantial increase in specific bioactivity following the 26-10 affinity purification step.

TABLE 1

Activity Yields of HIF Pre and Post-Affinity Purification using Monoclone Antidigoxin Ab 26-10

| Purification Steps | Prep. 2.6 (2 Kg tissue) | Prep. 2.7 (2 Kg tissue) | Prep. Pool 2 (1.4 Kg tissue) |
|---|---|---|---|
| Pre-Affinity CHP20 Column | 200 units (100 units/Kg tissue) | 500 units (250 units/Kg tissue) | 1200 units (857 units/Kg tissue) |
| Post-Affinity Semiprep. HPLC | 16,000 units (8000 units/Kg tissue) | 10,000 units (5000 units/Kg tissue) | 10,000 units (7143 units/Kg tissue) |
| Anal. HPLC | 14,000 units (7000 units/Kg tissue) | 8000 units (7000 units/Kg tissue) | 9000 units (6429 units/Kg tissue) |

Since the molecular weights of HIF and ouabain are identical (Tymiak et al., 1993), and since the affinity constants for binding to purified Na, K-ATPase are approximately the same for both inhibitors (~1 nM) (Haupert, G. T., Jr., Carilli, C. T., and Cantley, L. C., *Am. J. Physiol.* 247:F919–F924, (1984), units of inhibition (1 U=50% inhibition under standard conditions) can be converted into picomoles of ouabain-equivalent activity. In the RBC $^{86}Rb^+$ uptake assay, 1 U is approximately 0.75 pmol of ouabain or HIF. If each kg of starting hypothalamic tissue yields ~7000 units (Table 1), the following calculation can be made:

$$7000\ U \times 0.75\ pmol/U \times 584\ pg/pmol \div 10^6 = 3\ \mu g\ HIF$$

This yield is substantially greater than that afforded by our earlier methodology where no more than 1 μg HIF could be expected per 5 kg starting tissue (Tymiak et al., 1993), and many preps were significantly below even that.

This means that, using the 26-10 affinity purification coupled with semipreparative HPLC, as much as 15 μg HIF per 5 kg prep can be reproducibly purified, and used to further characterize HIF.

Example 2

Mass Spectrometry of Purified HIF

Figure 2:
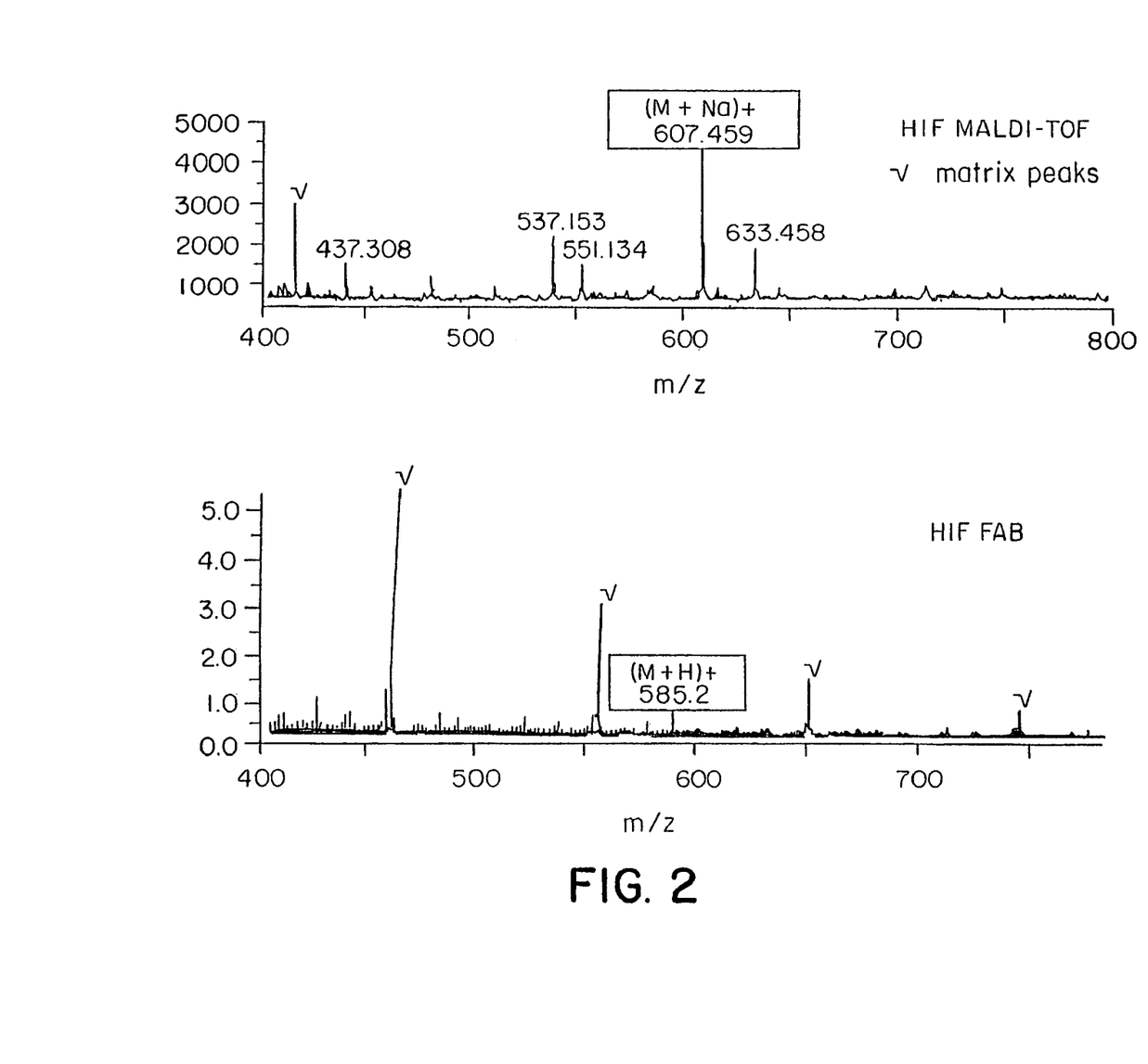
FIG. 2 are the results of mass spectrometry for determination of the molecular weight of the purified HIF.

To verify that the inhibitor purified using an anti-digoxin antibody was that isolated by the enzyme affinity technique (i.e., HIF), the molecular weight of the 26-10 purified material was determined by mass spectrometry. FIG. 2 shows a mass of 585 (M+H) by FAB, and 607 (M+Na$^+$) by MALDI-TOF, confirming the purified compound to be HIF (Tymiak, A. A., et al. *Proc. Natl. Acad. Sci., USA*, 90:8189–8193 (1993)).

Equivalents

Those skilled in the art will recognize, or be able to ascertain using no more than routine experimentation, many equivalents to the specific embodiments of the invention described herein. These and all other such equivalents are intended to be encompassed by the following claims.

What is claimed is:

1. A method of purifying hypothalamic inhibitory factor from a sample containing hypothalamic inhibitory factor comprising subjecting the sample to diafiltration, solid phase extraction and immunoaffinity chromatography.

2. The method of claim 1 wherein the diafiltration is in tandem to the solid phase extraction.

3. The method of claim 2 wherein the immunoaffinity chromatography follows the solid phase extraction.

4. A method of purifying hypothalamic inhibitory factor from a sample containing hypothalamic inhibitory factor comprising the steps of:
   a) subjecting the sample to diafiltration to produce a diafiltrate of hypothalamic inhibitory factor;
   b) subjecting the diafiltrate of a) to solid phase extraction to produce a first fraction of hypothalamic inhibitory factor;
   c) subjecting the first fraction of b) to immunoaffinity chromatography, wherein an antibody which binds to hypothalamic inhibitory factor or an HIF binding fragment thereof is coupled to an immunoaffinity column, to produce a second fraction of hypothalamic inhibitory factor;
   d) subjecting the second fraction of c) to reverse phase high pressure liquid chromatography to produce a third fraction of hypothalamic inhibitory factor; and
   e) recovering purified hypothalamic inhibitory factor from the third fraction of d).

5. The method of claim 4 wherein the diafiltration is continuous diafiltration.

6. The method of claim 5 wherein the continuous diafiltration is a tangential diafiltration.

7. The method of claim 4 wherein the solid phase extraction is performed using a C18 silica column and an acetonitrile elution.

8. The method of claim 4 wherein the sample is homogenized hypothalamus.

9. The method of claim 4 wherein the antibody is a monoclonal antibody or a binding fragment thereof having a binding affinity of from about $3 \times 10^{-7}$ M to about $5 \times 10^{-7}$ M for hypothalamic inhibitory factor.

10. The method of claim 9 wherein the monoclonal antibody or the binding fragment thereof has the binding affinity of monoclonal antibody 26-10, as deposited with ATCC under HB-8120, for hypothalamic inhibitory factor.

11. The method of claim 4 wherein the reverse phase high pressure liquid chromatography is performed by use of a C18 silica column and an acetonitrile gradient elution.

12. The method of claim 4 wherein the immunoaffinity chromatography of c) is performed using a methanol gradient.

13. A method of purifying hypothalamic inhibitory factor comprising the steps of:
   a) preparing a tissue slurry from a sample comprising hypothalamic inhibitory factor;
   b) obtaining a retentate of the sample of a), wherein the retentate comprises hypothalamic inhibitory factor;
   c) diafiltering the retentate of b) to produce a diafiltrate of hypothalamic inhibitory factor;
   d) chromatographically treating the diafiltrate of c) using solid phase extraction;
   e) performing immunoaffinity chromatography on the hypothalamic inhibitory factor obtained in d) using an antibody which binds to hypothalamic inhibitory factor or a hypothalamic inhibitory factor antibody binding fragment thereof;
   f) performing reverse phase high pressure liquid chromatography on the hypothalamic inhibitory factor obtained in e);
   thereby producing purified hypothalamic inhibitory factor.

14. The method of claim 13 wherein the diafiltration is continuous diafiltration.

15. The method of claim 14 wherein the continuous diafiltration is a tangential diafiltration.

16. The method of claim 13 wherein the solid phase extraction of d) is performed using a C18 silica column and an acetonitrile elution.

17. The method of claim 13 wherein the sample is homogenized hypothalamus.

18. The method of claim 13 wherein the antibody is a monoclonal antibody or a binding fragment thereof having a binding affinity of from about $3 \times 10^{-7}$ M to about $5 \times 10^{-7}$ M for hypothalamic inhibitory factor.

19. The method of claim 18 wherein the monoclonal antibody or the binding fragment thereof has the binding affinity of monoclonal antibody 26-10, as deposited with ATCC under HB-8120 for hypothalamic inhibitory factor.

20. The method of claim 13 wherein the reverse phase high pressure liquid chromatography of f) is performed by use of a C18 silica column and an acetonitrile gradient elution.

21. A method of purifying hypothalamic inhibitory factor comprising the steps of:
   a) performing tangential diafiltration on a sample comprising hypothalamic inhibitory factor to produce a diafiltrate permeate which includes the hypothalamic inhibitory factor;
   b) performing solid phase extraction on the diafiltrate permeate of a) to produce a concentrate of hypothalamic inhibitory factor;
   c) performing immunoaffinity chromatography on the concentrate of b) using an antibody having affinity for hypothalamic inhibitory factor or an hypothalamic inhibitory factor antibody binding fragment thereof to produce a hypothalamic inhibitory factor-containing fraction; and
   d) performing reverse phase high pressure liquid chromatography on the hypothalamic inhibitory factor-containing fraction of c) to produce purified hypothalamic inhibitory factor.

22. The method of claim 21 wherein the solid phase extraction of b) is performed using a C18 silica column and an acetonitrile elution.

23. The method of claim 21 wherein the sample is homogenized hypothalamus.

24. The method of claim 21 wherein the antibody is a monoclonal antibody or a binding fragment thereof having a binding affinity of from about $3 \times 10^{-7}$ M to about $5 \times 10^{-7}$ M for hypothalamic inhibitory factor.

25. The method of claim 24 wherein the monoclonal antibody the binding fragment thereof has the binding affinity of monoclonal antibody 26-10, as deposited with ATCC uner HB-8120, for hypothalamic inhibitory factor.

26. The method of claim 21 wherein the reverse phase high pressure liquid chromatography of d) is performed by use of a C18 silica column and an acetonitrile gradient elution.

27. A method of purifying hypothalamic inhibitory factor comprising the steps of:
   a) blending a tissue comprising hypothalamic inhibitory factor to form a tissue slurry;
   b) centrifuging the tissue slurry of a) to produce a retentate comprising the hypothalamic inhibitory factor;
   c) tangentially diafiltering the retentate of b) to produce a diafiltrate permeate comprising the hypothalamic inhibitory factor;
   d) chromatographically treating the diafiltrate permeate of c) by solid phase extraction employing an acetonitrile elution and a silica packing to produce a first hypothalamic inhibitory factor fraction in acetonitrile;
   e) concentrating the first hypothalamic inhibitory factor fraction of d);
   f) chromatographically treating the concentrated hypothalamic inhibitory factor of e) by immunoaffinity chromatography employing a glycine elution and a resin packing, wherein an antibody which binds to hypothalamic inhibitory factor or a hypothalamic inhibitory factor antibody binding fragment thereof is coupled to the resin, to produce a fraction of hypothalamic inhibitory factor in glycine;
   g) chromatographically treating the hypothalamic inhibitory factor of f) by reverse phase high pressure liquid chromatography employing an acetonitrile gradient elution and a silica packing to produce a second hypothalamic inhibitory factor fraction in acetonitrile;
   h) evaporating the acetonitrile from the second hypothalamic inhibitory factor fraction in acetonitrile of g) thereby producing purified hypothalamic inhibitory factor.

28. The method of claim 27 wherein the solid phase extraction of d) is performed using a C18 silica column and an acetonitrile elution.

29. The method of claim 27 wherein the sample is homogenized hypothalamus.

30. The method of claim 27 wherein the antibody is a monoclonal antibody or a binding fragment thereof having a binding affinity of from about $3 \times 10^{-7}$ M to about $5 \times 10^{-7}$ M for hypothalamic inhibitory factor.

31. The method of claim 30 wherein the monoclonal antibody or the binding fragment thereof has the binding affinity of monoclonal antibody 26-10, as deposited with ATCC under HB-8120, for hypothalamic inhibitory factor.

32. The method of claim 27 wherein the reverse phase high pressure liquid chromatography of g) is performed by use of a C18 silica column and an acetonitrile gradient elution.

33. A method of purifying hypothalamic inhibitory factor from a sample containing hypothalamic inhibitory factor comprising subjecting the sample to diafiltration and immunoaffinity chromatography.

34. A method of purifying hypothalamic inhibitory factor from a sample containing hypothalamic inhibitory factor comprising subjecting the sample to tangential diafiltration, solid phase extraction and immunoaffinity chromatography.

35. The method of claim 34 wherein the solid phase extraction is performed using a C18 silica column and an acetonitrile elution.

36. The method of claim 34 wherein the sample is homogenized hypothalamus.

37. The method of claim 34 wherein the immunoaffinity chromatography is performed using an antibody which binds to hypothalamic inhibitory factor or a hypothalamic inhibitory factor binding fragment thereof which is coupled to an immunoaffinity column.

38. The method of claim 37 wherein the antibody is a monoclonal antibody or a binding fragment thereof having a binding affinity of from about $3\times10^{-7}$ M to about $5\times10^{-7}$ M for hypothalamic inhibitory factor.

39. The method of claim 38 wherein the monoclonal antibody or the binding fragment thereof has the binding affinity of monoclonal antibody 26-10 as deposited with ATCC under HB-8120, for hypothalamic inhibitory factor.

40. The method of claim 34 wherein the immunoaffinity chromatography is performed using a methanol gradient.

\* \* \* \* \*